(12) United States Patent
Stroebech

(10) Patent No.: US 12,310,878 B2
(45) Date of Patent: May 27, 2025

(54) ALIGNMENT AID FOR ALIGNING A SENSOR PATCH TO A BASE PLATE

(71) Applicant: Coloplast A/S, Humlebaek (DK)

(72) Inventor: Esben Stroebech, Hoersholm (DK)

(73) Assignee: Coloplast A/S, Humlebaek (DK)

( * ) Notice: Subject to any disclaimer, the term of this patent is extended or adjusted under 35 U.S.C. 154(b) by 712 days.

(21) Appl. No.: 17/606,056

(22) PCT Filed: Apr. 23, 2020

(86) PCT No.: PCT/DK2020/050112
§ 371 (c)(1),
(2) Date: Oct. 25, 2021

(87) PCT Pub. No.: WO2020/216426
PCT Pub. Date: Oct. 29, 2020

(65) Prior Publication Data
US 2022/0249271 A1    Aug. 11, 2022

(30) Foreign Application Priority Data

Apr. 26, 2019 (DK) .......................... PA 2019 70263

(51) Int. Cl.
*A61F 5/44* (2006.01)
*A61F 5/443* (2006.01)
*G01N 19/04* (2006.01)

(52) U.S. Cl.
CPC ............ *A61F 5/4404* (2013.01); *A61F 5/443* (2013.01); *G01N 19/04* (2013.01)

(58) Field of Classification Search
CPC ........ A61F 5/4404; A61F 5/443; A61F 5/448; A61F 5/445; G01N 19/04
(Continued)

(56) References Cited

U.S. PATENT DOCUMENTS 4,294,252 A * 10/1981 Einset ...................... A61F 5/448
                                                      604/345
4,359,051 A * 11/1982 Oczkowski ............. A61F 5/448
                                                      604/339
(Continued)

FOREIGN PATENT DOCUMENTS

| CN | 104337618 A | 2/2015 |
|---|---|---|
| EP | 0598625 B1 | 1/1999 |

(Continued)

*Primary Examiner* — Catharine L Anderson
*Assistant Examiner* — Quynh Dao Le
(74) *Attorney, Agent, or Firm* — Coloplast Corp., Coloplast A/S; Nick Baumann

(57) ABSTRACT

An alignment aid for aligning a sensor patch (20) on a base plate (30) for an ostomy appliance, the alignment aid facilitates easy and precise alignment of the sensor patch on the base plate. The alignment aid comprises a sleeve (10) having a first surface comprising a first sleeve section (40) and a second sleeve section (50), the first sleeve section and the second sleeve section being connected along a connection line (60), said connection line defining a hinge enabling the first sleeve section to pivot and superimpose the second sleeve section. The first sleeve section is configured to secure the proximal side of sensor patch and the second sleeve section is configured to secure the distal side base plate. When the first sleeve section is pivoted to overly the second sleeve section, the sensor patch is transferred to the proximal surface of the base plate.

6 Claims, 2 Drawing Sheets

(58) Field of Classification Search
USPC .............. 604/327, 332, 336, 338, 339, 361; 602/57
See application file for complete search history.

(56) References Cited

U.S. PATENT DOCUMENTS

| | | | |
|---|---|---|---|
| 6,171,289 B1 | 1/2001 | Millot et al. | |
| 6,482,491 B1 | 11/2002 | Samuelsen et al. | |
| 8,409,703 B2 | 4/2013 | Burch | |
| 8,426,668 B2 | 4/2013 | Madsen et al. | |
| 8,957,277 B2 | 2/2015 | Carty et al. | |
| 9,775,385 B2* | 10/2017 | Stevenson | A41D 13/012 |
| 2007/0005032 A1 | 1/2007 | Shan et al. | |
| 2009/0216169 A1 | 8/2009 | Hansen et al. | |
| 2010/0030167 A1* | 2/2010 | Thirstrup | A61F 5/4404 |
| | | | 340/657 |
| 2011/0213321 A1* | 9/2011 | Fattman | A61F 5/443 |
| | | | 604/344 |
| 2012/0220967 A1 | 8/2012 | Lundholt et al. | |
| 2014/0303574 A1 | 10/2014 | Knutson | |
| 2015/0182383 A1 | 7/2015 | Carty et al. | |
| 2017/0128615 A1 | 5/2017 | Bartholomew et al. | |
| 2018/0133360 A1 | 5/2018 | Bingol et al. | |
| 2018/0289938 A1 | 10/2018 | Laux et al. | |
| 2018/0311066 A1 | 11/2018 | Hansen et al. | |
| 2018/0311363 A1 | 11/2018 | Takita et al. | |
| 2018/0360668 A1 | 12/2018 | Laulicht et al. | |
| 2020/0163792 A1* | 5/2020 | Schertiger | A61F 5/443 |
| 2021/0338471 A1* | 11/2021 | Nolan | A61F 5/448 |

FOREIGN PATENT DOCUMENTS

| | | |
|---|---|---|
| EP | 3056225 A1 | 8/2016 |
| WO | 03061720 A1 | 7/2003 |
| WO | 2007098762 A1 | 9/2007 |

* cited by examiner

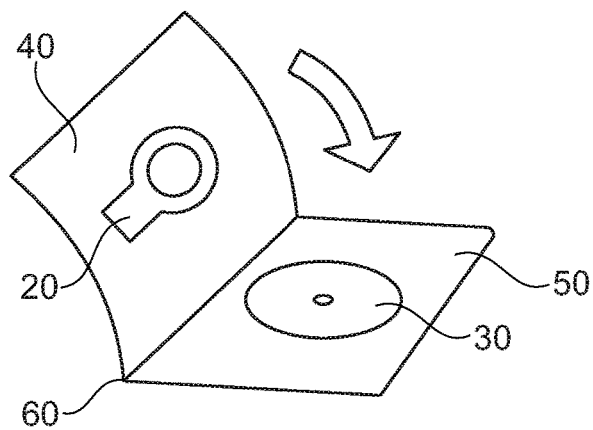
Fig. 3
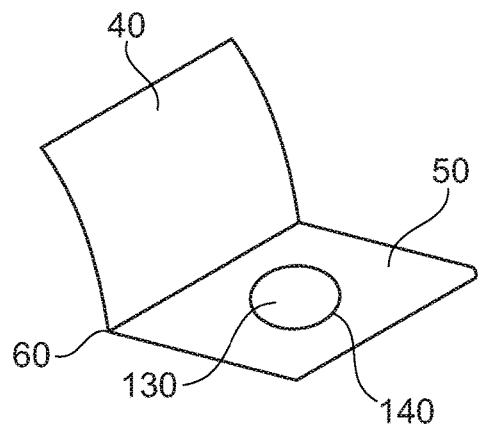
Fig. 4
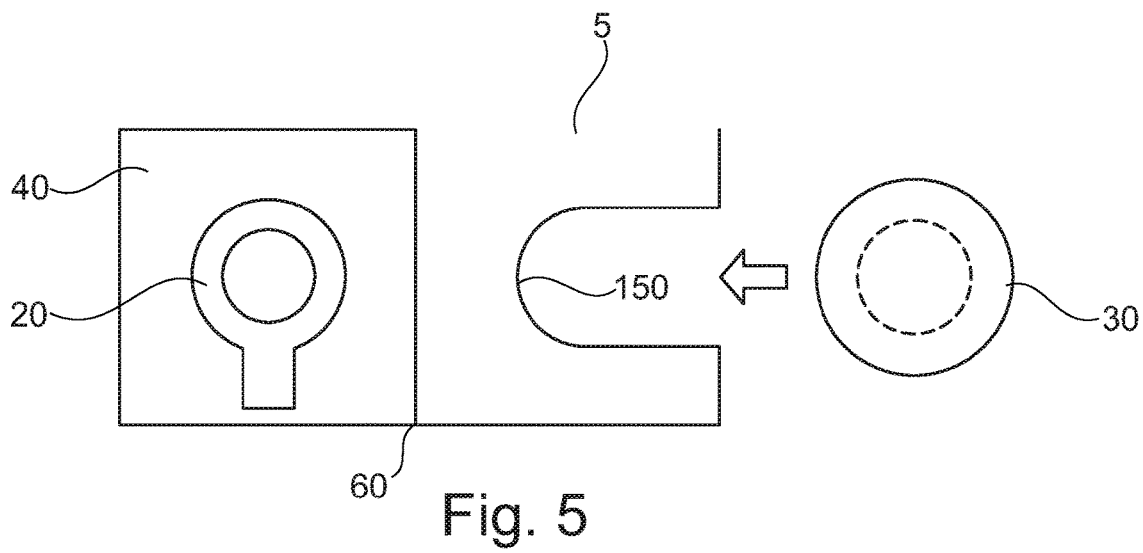
Fig. 5
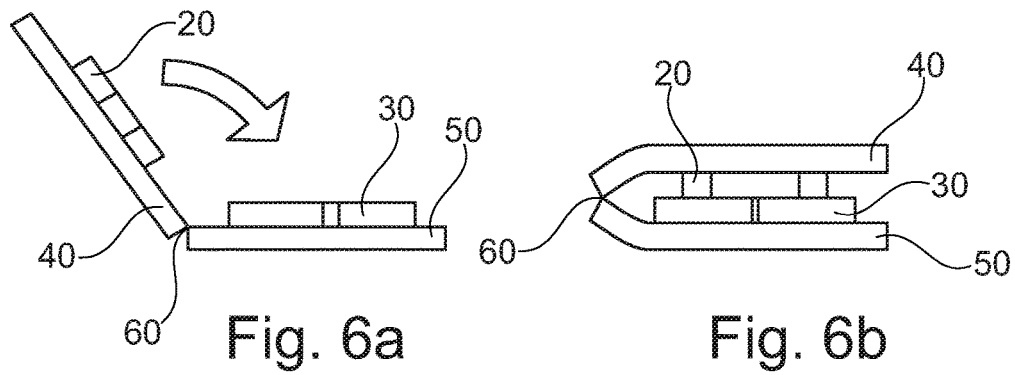
Fig. 6a
Fig. 6b
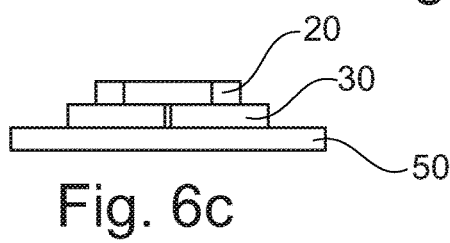
Fig. 6c

ALIGNMENT AID FOR ALIGNING A SENSOR PATCH TO A BASE PLATE The invention relates to an alignment aid for aligning a sensor patch on a base plate for an ostomy appliance, a kit of an alignment aid and a sensor patch, a kit of an alignment aid, a sensor patch and a base plate and a method of aligning such sensor patch to an ostomy base plate.

BACKGROUND

Stomal output often contains body fluids and visceral contents that are aggressive to both the skin of a user and to ostomy devices; these have a detrimental effect on the efficiency and integrity of the adhesive materials that are applied to attach the ostomy device to the user's skin surface. For users in general, safe, reliable and efficient ostomy devices are evidently highly desirable.

However, a particularly major and persistent concern of a large population of ostomists continues to be failure of the base plate adhesive attaching the ostomy appliance to the user's skin surface, because such failure almost inevitably leads to embarrassing and stigmatising leakage incidents. Such incidents in turn are known from several user interviews to lead to a reduced quality-of-life feeling. Adhesive failure of the base plate adhesive can result from various reasons. Most often, a leakage incident is caused by stomal output entering between the proximal surface of the base plate and the user's skin, e.g. due to less-than-optimal attachment of the base plate to the skin arising from e.g. uneven skin surface or skin folds. This undesirable progression of stomal output "underneath" the adhesive leads to deterioration and/or weakening of the adhesive material carrying the weight and providing the seal of the ostomy appliance. Often such failure happens surprisingly fast and is only detectable for the user once the failure has already become so severe that leakage occurs, requiring immediate change of the ostomy appliance and possibly also of the user's clothes.

In other instances, the primary factor of adhesive failure is simply a question of how much time has elapsed since the base plate of the ostomy appliance was first applied to the user's skin surface. In addition to the output from the stoma itself, the peristomal skin surface continuously secretes some moisture (e.g. sweat). To mitigate this, most often adhesives of base plates for ostomy devices include hydrocolloid materials which are capable of absorbing high levels of moisture, thereby stabilizing the polymer matrix of the adhesive material and prolonging the lifetime ("wear time") of the base plate. However, eventually the adhesion capability of the base plate no longer can support the force exerted on the base plate from the load of the output ostomy bag, and the appliance must be replaced.

As there can be considerable differences in the severity and/or speed by which adhesive failure and potentially leakage occur, and as these differences at least to some extent are correlated to various factors including those presented above, a mere indication that failure or leakage is imminent, or that it has already occurred, fails to represent a reliable and satisfactory solution to the problem of avoiding sudden embarrassing and stigmatising leakage incidents in ostomy appliances. In other words, the users of ostomy appliances could greatly benefit from an appliance solution which provides them with better guidance and options regarding how and—not least—how quickly to react to beginning failure or leakage of the adhesive of the base plate of the appliance. More generally, ostomists and health care professionals alike would welcome improvements in ostomy devices to reduce or eliminate the occurrence of sudden leakage incidents.

SUMMARY OF THE INVENTION

Disclosed is an alignment aid for aligning a sensor patch on a base plate for an ostomy appliance, the alignment aid facilitates easy and precise alignment of the sensor patch on the base plate. The alignment aid comprises a sleeve having a first surface comprising a first sleeve section and a second sleeve section, the first sleeve section and the second sleeve section being connected along a connection line, said connection line defining a hinge enabling the first sleeve section to pivot and superimpose the second sleeve section. The first sleeve section is configured to secure a proximal side of the sensor patch and the second sheet is configured to secure a distal surface of the base plate. When the first sleeve section is pivoted to overlay the second sleeve section, the sensor patch may be transferred to the proximal surface of the base plate.

BRIEF DESCRIPTION OF THE DRAWING

The accompanying drawings are included to provide a further understanding of embodiments and are incorporated into and are a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 3 illustrates an embodiment of an alignment aid in use and in perspective, FIG. 4 illustrates an embodiment of an alignment aid with a slit and through-going hole and FIG. 5 illustrates an embodiment of an alignment aid with a cut-out for securing a base plate.

FIG. 6a-6c show operation of an embodiment of an alignment aid.

DETAILED DESCRIPTION

Figure 1:
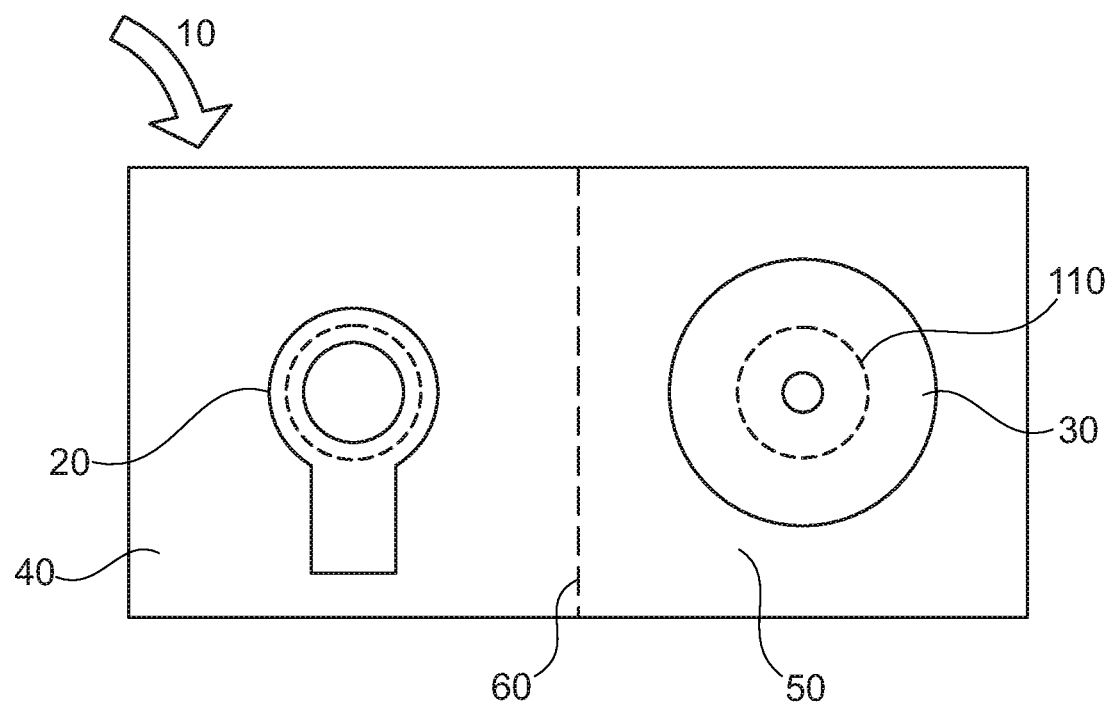
FIG. 1 illustrates an embodiment of an alignment aid seen from the first surface.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with respect to the orientation of the Figure(s) being described. Because components of embodiments can be positioned in a number of different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to the proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma, i.e. "across" the distal/proximal surface of the base plate. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The use of the word "essentially" as a qualifier to certain structural and functional features or effects in this disclosure is used for emphasizing what is the most important focus of something or fact about something (i.e. a feature may have or fulfil a variety of effects, but when the disclosure discusses one effect as being "essentially" provided, this is the focus and the most important effect in relation to the disclosure).

Throughout the disclosure, the use of the terms "first", "second", "third", "fourth", "primary", "secondary", "tertiary" etc. does not imply any particular order or importance but are included merely to identify individual elements. Furthermore, the labelling of a first element does not imply the presence of a second element and vice versa.

Embodiments relates to an alignment aid for aligning a sensor patch on a base plate for an ostomy appliance, the alignment aid comprises a sleeve having a first surface comprising a first sleeve section and a second sleeve section, the first sleeve section and the second sleeve section being connected along a connection line, said connection line defining a hinge enabling the first sleeve section to pivot and superimpose the second sleeve section, the first sleeve section is configured to secure a proximal side of a sensor patch and the second sheet is configured to secure a distal side of a base plate, wherein the first sleeve section is at least the size of the base plate and the first sleeve section is provided with a release surface.

Embodiments further relates to a kit comprising an alignment aid for aligning a sensor patch on a base plate for an ostomy appliance and a sensor patch, the alignment aid comprises a sleeve having a first surface comprising a first sleeve section and a second sleeve section, the first sleeve section and the second sleeve section being connected along a connection line, said connection line defining a hinge enabling the first sleeve section to pivot and superimpose the second sleeve section, the first sleeve section is configured to secure a proximal side of sensor patch and the second sheet is configured to secure a distal side of a base plate, the sensor patch comprising a distal side and a proximal side having an adhesive layer, the distal side being at least partly adapted for attachment to an adhesive surface of the base plate and the proximal side adapted to adhere to the skin, wherein the first sleeve section is at least the size of the base plate and the first sleeve section is provided with a release surface.

Embodiments still further relates to kit comprising an alignment aid for aligning a sensor patch on a base plate for an ostomy appliance, a sensor patch and a base plate for an ostomy appliance, the alignment aid comprises a sleeve having a first surface comprising a first sleeve section and a second sleeve section, the first sleeve section and the second sleeve section being connected along a connection line, said connection line defining a hinge enabling the first sleeve section to pivot and superimpose the second sleeve section, the first sleeve section is configured to secure a proximal side of a sensor patch and the second sheet is configured to secure a distal side of a base plate, the sensor patch comprising a distal side and a proximal side having an adhesive layer, the distal side being at least partly adapted for attachment to an adhesive surface of the base plate and the proximal side adapted to adhere to the skin, the base plate comprises a proximal surface having an adhesive layer being adapted for attachment of the base plate to the skin surface of a user, and a distal surface facing away from the skin, wherein the first sleeve section is at least the size of the base plate and the first sleeve section is provided with a release surface.

When addressing securing a base plate to the alignment aid, the base plate may be directly secured to the second sleeve section or it mat be indirectly secured to the second sleeve section. For example, when using a one-piece appliance, the base plate may be secured via the ostomy bag.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. For example, the base plate may comprise a coupling ring for coupling an ostomy pouch to the base plate. Further, a two-part ostomy appliance may facilitate correct application of the base plate to skin, e.g. to an improved user sight of the stomal region. Alternatively, the ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The base plate may comprise a first adhesive layer, i.e. a first layer of an adhesive material. During use, a proximal surface of the first adhesive layer adheres to the user's skin in the peristomal area and/or to additional seals, such as sealing paste, sealing tape and/or sealing ring. The first adhesive layer may be made of a first composition. The first composition may comprise one or more polyisobutenes and/or styrene-isoprene-styrene. The first composition may comprise one or more hydrocolloids. The first composition may comprise one or more water soluble or water swellable hydrocolloids. The first composition may be a pressure sensitive adhesive composition suitable for medical purposes comprising a rubbery elastomeric base and one or more water soluble or water swellable hydrocolloids. The first adhesive layer may comprise a distal surface and a proximal surface. The proximal surface of the first adhesive layer may be configured to adhere to the user's skin. The distal surface of the first adhesive layer may be configured to face away from the skin of the user.

The first adhesive layer may form the adhesive surface of the base plate adapted for attachment of the base plate to the skin surface of the user. The first adhesive layer may form part of the adhesive surface of the base plate adapted for attachment of the base plate to the skin surface of the user.

The base plate may comprise a second adhesive layer, i.e. a second layer of an adhesive material, also denoted rim adhesive layer. The second adhesive layer may be of a different adhesive material than the first adhesive layer. The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids. The second composition may be a pressure sensitive adhesive composition suitable for medical purposes comprising a rubbery elastomeric base and one or more water soluble or water swellable hydrocolloids. The second adhesive layer may comprise a distal surface and a proximal surface. The proximal surface of the second adhesive layer may be configured to adhere to the user's skin, e.g. at least at a rim portion of the second adhesive layer. The distal surface of the second adhesive layer may be configured to face away from the skin of the user. The second adhesive layer may be covering a larger area than the first adhesive layer, e.g. such that the proximal surface of the second adhesive layer forms an adhesive rim surrounding the first adhesive layer.

The sensor patch is adapted for attachment to the base plate. For example, the sensor patch may be configured to be positioned between the skin of the user and the proximal side of the base plate. For example, the sensor patch may be adapted for attachment to the first adhesive layer of the base plate. For example, a distal side of the sensor patch may be configured to be facing the proximal surface of the first adhesive layer of the base plate. For example, the sensor patch, such as a distal side of the sensor patch may be configured to adhere to the proximal surface of the first adhesive layer of the base plate.

The sensor patch may comprise a stomal opening and/or the sensor patch may be adapted to form a stomal opening. Each layer of the sensor patch, as described below, may comprise stomal openings and/or be adapted to form a stomal opening for collectively forming the stomal opening of the sensor patch. The stomal opening of the sensor patch may be configured to be aligned with the stomal opening of the base plate, such as to collectively form the stomal opening of the combined base plate and sensor patch. The size and/or shape of the stomal opening of the sensor patch may be adjusted by the user or nurse before application of the sensor patch to accommodate the user's stoma. The size and/or shape of the stomal opening of the sensor patch may be adjusted together with adjustment of the stomal opening of the base plate, e.g. after the sensor patch has been attached to the base plate. The stomal opening(s) may have a centre point.

The sensor patch may comprise a sensor assembly. The sensor assembly may form a sensor assembly layer. The sensor assembly may have a distal side and a proximal side. The sensor patch may be configured to be positioned on the base plate such that the distal surface of the sensor assembly is coupled to the proximal adhesive surface of the base plate.

The sensor assembly may comprise a plurality of electrodes. The plurality of electrodes may include a first electrode and a second electrode for forming a first sensor. The plurality of electrodes may include a third electrode, a fourth electrode, a fifth electrode and/or a sixth electrode. The first electrode may be a common ground electrode. For example, a second sensor may be formed by the first electrode and the third electrode, a third sensor may be formed by the first electrode and the fourth electrode, a fourth electrode may be formed by the first electrode and the fifth electrode, and/or a fifth electrode may be formed by the first electrode and the sixth electrode. Each electrode may have respective connection parts for connecting the electrodes to respective terminal elements of a monitor device.

The plurality of electrodes is electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The plurality of electrodes may form loops and/or open loops. Open loop electrode(s) enables electrode arrangement in few or a single electrode layer.

The sensor assembly may comprise a support layer, e.g. with a proximal surface and a distal surface. The plurality of electrodes may be provided, such as formed, on the proximal surface of the support layer, e.g. the plurality of electrodes may be positioned on the proximal surface of the support layer.

The sensor assembly may comprise a masking element, e.g. with a proximal surface and a distal surface. The masking element may be configured to electrically insulate at least parts of the plurality of electrodes from proximal layers, such as a first adhesive sensor layer. The masking element may cover or overlap parts of the plurality electrodes, e.g. when seen in the axial direction.

The sensor patch may comprise a first adhesive sensor layer, e.g. with a proximal side and a distal side. The first adhesive sensor layer may be arranged on a proximal side of the sensor assembly. The first adhesive sensor layer, such as the proximal side of the first adhesive sensor layer, may form the proximal side of the sensor patch. The proximal side of the first adhesive sensor layer may be configured to adhere to the user's skin. Thus, after being applied to the base plate, the combined base plate and sensor patch may form an adhesive proximal surface configured to be applied to the skin surface of the user. The first adhesive sensor layer may be made of a first adhesive sensor material, such as the first composition, the second composition or a third composition. The third composition may comprise one or more polyisobutenes and/or styrene-isoprene-styrene. The third composition may comprise one or more hydrocolloids. The third composition may comprise one or more water soluble or water swellable hydrocolloids. The third composition may be a pressure sensitive adhesive composition suitable for medical purposes comprising a rubbery elastomeric base and one or more water soluble or water swellable hydrocolloids.

The sensor patch is adapted to form a stomal opening with a centre point. The stomal opening is configured to allow passage of output through the stomal opening and into an ostomy pouch attached to the base plate.

Arranging the sensor patch correctly on the base plate can be difficult for the user. It is important that the sensor patch is oriented correctly, with the distal side facing the base plate and the proximal side facing the skin of the user. If the sensor is applied wrongly, with the distal side facing the skin, several problems may arise. The sensors will not work properly as they do not face the skin surface the way they are configured to, and the base plate may not adhere properly to the skin as the distal side of the sensor patch may not comprise the same adhesive properties as the proximal side—or it may even be non-adhesive. This may result in undesired leakage.

As the sensor patch may allow electronic measurements of performance of the base plate and/or to facilitate detection of increasing risks of leakage and/or to facilitate detection of decreasing adherence of the base plate to the skin of the user, it is important that the sensor patch is oriented correctly. Electrodes need to be positioned correctly in order to perform its function and if the sensor patch may be oriented wrongly then for example the electrodes may be embedded in adhesive instead of being in contact with the skin which evidently will lead to false measurements. A fool-proof way of aligning the sensor patch correctly on the base plate is desired.

In aspects, an alignment aid helping the user to align the sensor patch correctly to the base plate is provided.

In embodiments, the first sleeve section has a size that substantially equals the second sleeve section.

In embodiments, the force needed for releasing the sensor patch from the first sleeve section is lower than the force needed for releasing the sensor patch from the base plate. Hence, when contacting the distal side of the sensor patch with the proximal adhesive surface of the base plate, as may happen when the first sleeve section overlays the second sleeve section, the sensor patch will be attached to the base plate. When the first sleeve section then is pulled away from the second sleeve section, the sensor patch will release from the first sleeve section and the sensor patch is now transferred to the base plate.

In embodiments, the first sleeve section may not be removed from the combined sensor patch and base plate until before the base plate is to be applied to the skin, the first sleeve section may in that situation serve as a release liner protecting the adhesive surface of the combined base plate and sensor patch. Before application to the skin, the alignment aid is removed.

In embodiments, the sleeve is less flexible than the sensor patch. The sleeve may comprise a relatively stiff layer in order to stabilize the configuration of the sensor patch and secure good alignment when the sensor patch is combined with the base plate. In embodiments, the sensor patch may at least partly comprise very soft and/or thin structures that may be difficult to handle without a supporting structure.

In embodiments, the sensor patch is attached directly to first sleeve section by the proximal side of the sensor patch. Hence, the first sleeve section may serve as a release liner for the sensor patch, protecting the adhesive side of it.

In embodiments, the base plate is attached to the second sleeve section by adhesive means. The adhesive means may for example be spots or lines on the second sleeve section having adhesive properties capable of holding the base plate in place when it is in contact with these. In embodiments, the adhesive means is easily releasable from the base plate.

In embodiments, the second sleeve section is provided with a recess that is able to accommodate at least a part of the base plate. For example, the second sleeve section comprises an embossed portion into which the base plate may fit and is secured in a fixed position.

In embodiments, the second sleeve section is provided with a through-going hole. The hole may help to correct alignment of the base plate when it is secured to the second sleeve section. In embodiments, the hole has a size approximately corresponding to an opening in the base plate. In embodiments, the size of the hole corresponds to a coupling means for an ostomy bag on the distal surface of the base plate. When the coupling means fit in the hole, the base plate is fixed in position at the second sleeve section.

In embodiments, the second sleeve section comprises one or more breakable lines that facilitates that the user can remove portion(s) of the second sleeve section, thereby creating a through-going hole in the second sleeve section. The lines may for example be in the form of kiss-cut lines or perforated lines. In embodiments, the breakable lines are in the form of concentric circles, thereby facilitating that the size through-going can be adapted to fit different sizes or types of baseplates.

In embodiments, the second sleeve section is provided with a through-going hole corresponding to a protruding part of the base plate, such as when the base plate is designed for application to a protruding stoma. A protruding part of the base plate may fit as a plug in a hole and will stay in place facilitating a precise application of the sensor patch. In embodiments, the second sleeve section is provided with a slit or a cut-out facilitating easy insertion of a base plate.

By the phrase "securing" the base plate, respective the sensor patch to the alignment aid, is meant that the base plate and/or the sensor patch is temporarily maintained in the alignment aid in a way where its position on the alignment aid is fixed. Hence, the base plate and the sensor patch are releasably secured to the alignment aid.

In embodiments, the sensor patch is provided with a protective cover layer on the distal side to be removed before application of the sensor patch to the base plate. The protective cover protects the delicate structure of the sensor patch as well as it may stabilize the sensor patch in case it comprises a soft or thin structure.

The base plate may comprise a release liner covering the proximal surface. The release liner protects the adhesive surface before use and is removed before aligning the sensor patch to the base plate.

In embodiments, the first sleeve section comprises markings showing the correct placement of the sensor. This facilitates correct positioning of the sensor patch on the first sleeve section.

In embodiments, the second sleeve section comprises markings or guide means showing the correct placement of the base plate or ostomy bag attached to base plate (one-piece). This facilitates correct positioning of the base plate on the second sleeve section.

The alignment aid is a tool for facilitating correct alignment of a sensor patch to a base plate. In embodiments, it can be in the form of a kit where the sensor patch and base plate are attached to the sleeve and the user will only have to remove optional release liners and cover layer before combining the sensor patch and the base plate and then applying the combined structure to the skin surrounding a stoma. In embodiments, the alignment aid is delivered with the sensor patch arranged om the first sleeve section and allowing the user to mount the base plate on the second sleeve section himself. This facilitates that the user can use different base plates with the same alignment aid. In embodiments, the alignment aid is delivered without the sensor patch and the base plate, so the user can pick the sensor patch and base plate himself and arrange them at the alignment aid in a personalized way. In embodiments, the alignment aid can be used repeatedly, not only being a single use tool.

In embodiments, the connection line is in the form of a perforated line or weakened line. The connection line may be in any form that makes the sleeve have a preference for bending sharply along the connection line when the sleeve is bended along this line.

In embodiments, the first sleeve section and the second sleeve section are separable along the connection line. This allows removal of the second sleeve section after combining the sensor patch and the base plate and leaving the combined structure on the first sleeve section serving as release liner until use.

For easy grabbing of the first or second sleeve section, the sleeve may in embodiments be provided with one or more tab members.

In embodiments, the distal side of the sensor patch is non-adhesive. In embodiments, the sensor patch may be provided with a top film on the distal side. As the sensor patch is adhered to the base plate by the adhesive layer of the base plate, no adhesive is needed. Furthermore, in the case that the sensor patch is extending further than the base plate, not being fully covered by the base plate, a non-adhesive distal side may be advantageous in order not to stick to the clothes of the user.

In embodiments, the sensor patch comprises a central section and a peripheral section. In embodiments, the central section is provided with a stomal opening. When the sensor patch is applied to a base plate, the stomal opening may be arranged substantially concentric to a stomal opening in the base plate, the opening being accommodated for receiving a stoma. In embodiments, the central section has a substantially circular or oval shape.

In embodiments, the peripheral section is extending radially away from the central section. The peripheral section may encircle the central section, or it may extend radially outwards, in one or more directions, from the central section. In embodiments, the peripheral section comprises an elongated shape and extends radially outwards in one direction from the central section. The peripheral section may extend further than the outer rim of the base plate when the sensor patch is applied to such base plate, thereby leaving a part of the peripheral section unattached to the base plate.

In embodiments, the central section comprises a first adhesive and the peripheral section comprises a second adhesive. In embodiments, the first adhesive and the second adhesive are the same adhesive. In embodiments the first adhesive and the second adhesive may have different properties. For example, the adhesives may differ with respect to adhesive tack and/or softness.

Embodiments relates to a method of aligning a sensor patch on an ostomy base plate comprising the steps of: providing an ostomy base plate comprising a proximal surface having an adhesive layer being adapted for attachment of the base plate to the skin surface of a user, and a distal surface facing away from the skin, providing a sensor patch comprising a distal side and a proximal side having an adhesive layer, the distal side being at least partly adapted for attachment to an adhesive surface of the base plate and the proximal adhesive side adapted to adhere to the skin, providing an alignment aid comprising a sleeve with a first surface comprising a first sleeve section and a second sleeve section, the first sleeve section and the second sleeve section being connected along a connection line, said connection line defining a hinge enabling the first sleeve section to pivot and superimpose the second sleeve section, securing the base plate to the second sleeve section, securing the sensor patch to the first sleeve section, removing optional release liner from base plate, removing optional cover layer from sensor patch, pivot the sleeve so the first sleeve section superimposes the second sleeve section and the distal surface of the sensor patch is brought in contact with the proximal surface of the base plate.

Following these steps, the combined sensor patch and base plate can then be applied to the skin around a stoma of a patient.

Embodiments, and features of the various exemplary embodiments described in this application, may be combined with each other ("mixed and matched"), unless specifically noted otherwise.

DETAILED DESCRIPTION OF THE DRAWING

Figure 2:
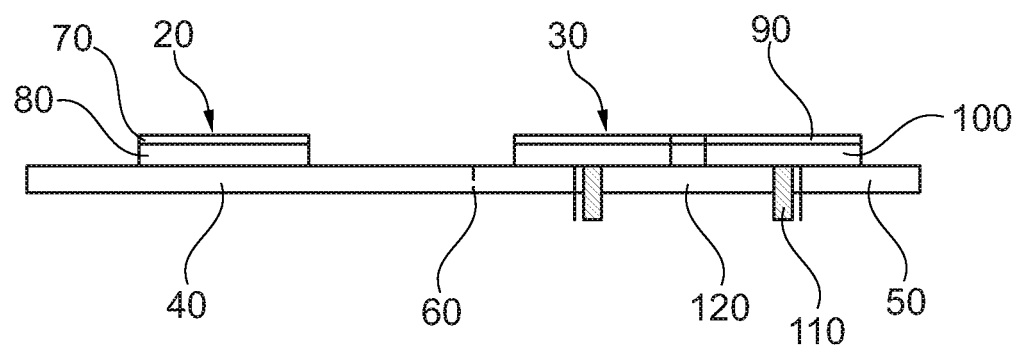
FIG. 2 illustrates the embodiment of FIG. 1 in cross-section.

FIGS. 1 and 2 show an embodiment of an alignment aid comprising a sleeve (10) with a sensor patch (20) and a base plate (30). The sensor patch (20) is secured to a first sleeve section (40) and the base plate (30) is secured to a second sleeve section (50). The first sleeve section (40) and the second section (50) are connected along a connection line (60). The sensor patch may comprise a top film (70) on the distal side and an adhesive layer (80) on the proximal side. The base plate comprises a proximal surface having an adhesive layer (90) and a distal surface (100), the distal surface (100) being provided with coupling means (110) for attaching a ostomy bag (not shown). The second sleeve section (50) comprises a through-going hole (120) for receiving the coupling means (110) and securing the base plate (30) in a fixed position on the alignment aid.

In FIG. 3, is shown an alignment aid where the first sleeve section (40) is pivoted along the connection line (60) to superimpose and overlay the second sleeve section (50), thereby combining the sensor patch (20) with the base plate (130). In FIG. 4 is another embodiment of an alignment aid where the second sleeve section (50) comprises a through-going hole (120) and a slit (140) for entering the base plate (30). In FIG. 5 is shown an embodiment of an alignment aid where the second sleeve section (50) comprises a cut-out (150) for securing a base plate (30).

FIGS. 6*a*-6*c* show operation of an alignment aid, conducting transferral of the sensor patch (20) to the base plate (30) by pivoting the alignment aid along the connection line (60) to let the first sleeve section (40) overlay the second sleeve section (50). When the base plate (30) and the sensor patch (20) are brought into contact with each other's, the alignment aid may stay on until application of the base plate (30) to the skin or the first sleeve section (40) may be detached from the second sleeve section (50) along the connection line (60) and the second sleeve section (50) may serve as a release liner protecting the adhesive surface until application to the skin.

The invention claimed is:

1. An alignment aid for aligning an ostomy sensor with an ostomy appliance, the alignment aid comprising:
    a sleeve having a first sleeve section and a second sleeve section, the first sleeve section and the second sleeve section connected along a connection line, with the connection line defining a hinge adapted to allow the first sleeve section to pivot and overlay the second sleeve section;
    a release surface applied to the first sleeve section;
    an adhesive proximal side of a sensor patch positioned on the release surface of the first sleeve section with a distal side of the sensor patch oriented to face away from the first sleeve section; and
    an opening formed in the second sleeve section, where the opening is sized to receive an ostomy bag coupling device connected to a distal side of a base plate and orient an adhesive proximal side of the base plate upward away from the second sleeve section;
    wherein, when the first sleeve section pivots about the hinge, the distal side of the sensor patch is coupled to the adhesive proximal side of the base plate and the first sleeve section is positioned as an outermost layer that removably covers the adhesive proximal side of a sensor patch.

2. The alignment aid of claim 1, wherein the connection line is a perforated line formed through a thickness of the sleeve.

3. The alignment aid of claim 1, wherein the opening is a circular through-going hole.

4. The alignment aid of claim 1, wherein the opening is a U-shaped cut-out formed in a side edge of the second sleeve section.

5. The alignment aid of claim 1, wherein the first sleeve section is a release liner that removably covers the adhesive proximal side of a sensor patch and the adhesive proximal side of the base plate.

6. The alignment aid of claim 1, wherein the distal side of the sensor patch is adhesively coupled to the adhesive proximal side of the base plate, and a force required to remove the first sleeve section from the adhesive proximal side of a sensor patch is less than a force required to remove the distal side of the sensor patch from the adhesive proximal side of the base plate.

* * * * *